(12) United States Patent
Kim

(10) Patent No.: US 7,819,809 B2
(45) Date of Patent: Oct. 26, 2010

(54) DEVICE FOR PIVOTING AN ULTRASOUND ELEMENT ASSEMBLY OF A PROBE IN AN ULTRASONIC DIAGNOSIS APPARATUS

(75) Inventor: Seong Rae Kim, Anyang-si (KR)

(73) Assignee: Medison Co., Ltd., Hongchun-gun (KR)

( * ) Notice: Subject to any disclaimer, the term of this patent is extended or adjusted under 35 U.S.C. 154(b) by 1058 days.

(21) Appl. No.: 11/228,289

(22) Filed: Sep. 19, 2005

(65) Prior Publication Data

US 2006/0173330 A1    Aug. 3, 2006

(30) Foreign Application Priority Data

Dec. 29, 2004    (KR) .................... 10-2004-0115713

(51) Int. Cl.
*A61B 8/00* (2006.01)
(52) U.S. Cl. ........................................... 600/459
(58) Field of Classification Search ............ 600/437, 600/441, 445–446, 459, 462–463; 73/619, 73/621, 633; 74/592, 97.2, 137, 551.3, 582
See application file for complete search history.

(56) References Cited

U.S. PATENT DOCUMENTS

| | | | |
|---|---|---|---|
| 4,106,492 A * | 8/1978 | Schuette et al. ............. | 600/446 |
| 4,231,373 A * | 11/1980 | Waxman et al. ............. | 600/446 |
| 4,483,326 A * | 11/1984 | Yamaka et al. ............. | 600/149 |
| 4,756,313 A * | 7/1988 | Terwilliger .................. | 600/462 |
| 4,893,628 A * | 1/1990 | Angelsen .................... | 600/441 |
| 4,930,515 A * | 6/1990 | Terwilliger .................. | 600/462 |
| 5,048,529 A * | 9/1991 | Blumenthal .................. | 600/446 |
| 5,088,495 A * | 2/1992 | Miyagawa .................... | 600/446 |
| 5,398,691 A * | 3/1995 | Martin et al. ................ | 600/463 |
| 5,402,789 A * | 4/1995 | Dow et al. .................... | 600/446 |
| 5,465,724 A * | 11/1995 | Sliwa et al. .................. | 600/459 |
| 5,575,288 A * | 11/1996 | Sliwa et al. .................. | 600/445 |
| 5,771,896 A * | 6/1998 | Sliwa et al. .................. | 600/462 |
| 6,471,653 B1 * | 10/2002 | Jordfald et al. .............. | 600/462 |
| 6,478,743 B1 * | 11/2002 | Jordfald et al. .............. | 600/462 |

FOREIGN PATENT DOCUMENTS

| | | |
|---|---|---|
| EP | 1 208 800 A2 | 5/2002 |
| JP | 4-236839 | 8/1992 |

OTHER PUBLICATIONS

Patent Abstracts of Japan, JP 06-006953, Jan. 14, 1994.

* cited by examiner

*Primary Examiner*—Eric F Winakur
*Assistant Examiner*—Lawrence N Laryea
(74) *Attorney, Agent, or Firm*—Oblon, Spivak, McClelland, Maier & Neustadt, L.L.P.

(57) ABSTRACT

The present invention relates to a device for pivoting an ultrasound element assembly of a probe in an ultrasonic diagnosis apparatus. A pivot shaft is rotatably coupled to a base and supports the ultrasound element assembly. A wire holder is coupled to the pivot shaft. A driving motor is mounted to the base and has a driving shaft. A wire rope assembly includes a housing connected to the driving shaft of the driving motor to be rotated together therewith, an elastic member provided in the housing, and a pair of wire ropes, a first end of each wire rope being connected to the wire holder and a second end of each wire rope being connected to the elastic member.

8 Claims, 9 Drawing Sheets

DEVICE FOR PIVOTING AN ULTRASOUND ELEMENT ASSEMBLY OF A PROBE IN AN ULTRASONIC DIAGNOSIS APPARATUS

FIELD OF THE INVENTION

The present invention generally relates to an ultrasonic diagnosis apparatus, and more particularly to a device for pivoting an ultrasound element assembly of a probe in an ultrasonic diagnosis apparatus.

BACKGROUND OF THE INVENTION

An ultrasonic diagnosis apparatus is a medical equipment for obtaining an ultrasound image of a target region in an object so as to provide clinical information of the target region, such as lesion or neoplasm information of internal organs, fetus information and the like. Typically, the ultrasonic diagnosis apparatus comprises at least one probe having an ultrasound element assembly for radiating the ultrasonic wave to the target region and receiving the echo signal reflected from the target region. Recently, to obtain more accurate diagnosis, there have been developed techniques for acquiring a 3-dimensional (3D) ultrasound image by pivoting the ultrasound element assembly of the probe.

Japanese Patent Application Publication No. 2002-153464 discloses a prior art probe of a 3D ultrasonic diagnosis apparatus, which will be described with reference to FIGS. 1A and 1B. FIG. 1A is a partial cross-sectional view showing an inner structure of a prior art probe for acquiring a 3D ultrasound image. FIG. 1B is a side view showing a power transmitting structure of a prior art probe.

As shown in the drawings, a prior art probe 1 comprises a case 10 having an opened top and a cover 12, which is coupled to the opened top of the case 10 and is adapted to contact an object to be examined (e.g., a body of a patient). A base 20 is contained in the case 10. A transducer 30 for supporting an ultrasound element assembly (not shown) is pivotably mounted to the base 20 by a pivot shaft 32. A driving motor 40 for generating power necessary for pivoting the transducer 30 and means for transmitting the power from the motor 40 to the pivot shaft 32 are mounted to the base 20.

The pivot shaft 32 is arranged horizontally and is rotatably coupled to the base 20 by bearings 34 at both ends of the shaft 32. Preferably, the driving motor 40 is a step motor and is mounted to an outer surface of the base 20. A driving shaft 42 of the motor 40 is inserted horizontally into the base 20 and supported by a bearing 44 at its end.

In order to transmit the power from the motor 40 to the pivot shaft 32, a driving pulley 46 is coupled to the driving shaft 42 for rotation with the shaft 42. A driven pulley 48 is coupled to the pivot shaft 32 for rotation with the shaft 32. The driving pulley 46 and the driven pulley 48 are arranged in alignment with each other and are connected by a driving belt 49. Preferably, the driving belt 49 is a flat strip having a rectangular cross-section.

When the driving pulley 46 rotates in a direction of arrow A depicted in FIG. 1B by the operation of the driving motor 40, the driven pulley 48 also rotates in a direction of arrow A by the driving belt 49. On the contrary, when the driving pulley 46 rotates in a direction of arrow B, the driven pulley 48 rotates in a direction of arrow B by the driving belt 49. Accordingly, the pivot shaft 32, to which the driven pulley 48 is coupled, and the transducer 30 supporting the ultrasound element assembly can be pivoted within a predetermined angle.

However, during the pivoting operation, the pulleys and the belt may slip, which hinders the driving force of the motor from being transmitted perfectly to the transducer. Further, since the operational vibration of the motor directly affects the transducer through the belt, the ultrasonic wave is radiated irregularly and the 3D ultrasound image may not be optimal. Thus, the image quality is degraded, which causes an erroneous diagnosis.

Also, the driving belt may get loosened due to the repeated operations, which makes it impossible to conduct the precise pivoting of the transducer. Although an additional belt tensioning means may be provided in the probe to solve this problem, the limited size of the probe imposes many limitations upon installing the belt tensioning means.

SUMMARY OF THE INVENTION

It is an object of the present invention to provide a device for pivoting an ultrasound element assembly of a probe, which transmits perfectly the driving force of a motor to an ultrasound element assembly, thereby achieving a high image quality.

In accordance with an aspect of the present invention, there is provided a device for pivoting an ultrasound element assembly of a probe in an ultrasonic diagnosis apparatus, the probe including a base for supporting the ultrasound element assembly, the device comprising: a pivot shaft, which is rotatably coupled to the base and supports the ultrasound element assembly; a wire holder, which is coupled to the pivot shaft; a driving motor, which is mounted to the base, the driving motor having a driving shaft; and a wire rope assembly, which includes a housing connected to the driving shaft of the driving motor to be rotated together therewith, an elastic member provided in the housing, and a pair of wire ropes, a first end of each wire rope being connected to the wire holder and a second end of each wire rope being connected to the elastic member.

The elastic member is a torsion coil spring. The torsion coil spring has bending portions at its both ends, the bending portions being exposed outside the housing and the second ends of the wire ropes being hitched respectively by the bending portions. The pair of wire ropes are arranged to cross with each other.

A speed reduction means is provided between the driving motor and the wire rope assembly. The speed reduction means includes: a driving pulley, which is coupled to the driving shaft of the driving motor; a driven pulley, which is fixed to the base; a timing belt, which is wound around the driving pulley and the driven pulley; and a driven shaft, one end of which is fixed to the driven pulley and the other end of which is fixed to the housing of the wire rope assembly.

A motor supporting plate is coupled to the driving motor (near the driving shaft of the driving motor) for fixing the driving motor to the base. The motor supporting plate has means for adjusting a tension of the timing belt by adjusting the distance between the driving pulley and the driven pulley.

The means for adjusting the tension of the timing belt includes: at least one through-hole, through which a bolt is fastened to fix the motor supporting plate to the base; extending portions, which extend vertically from the motor fixing plate; bending portions, which are formed horizontally at the tips of the respective extending portions; and bolt-holes, which are formed vertically at the bending portions. As bolts are tightened through the bolt-holes toward the base, a front end of each bolt moves to be in contact with the base and a reactional force against the movement of the bolt is applied to the motor supporting plate, thereby causing the driving pulley to move away from the driven pulley.

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PRESENT INVENTION

Figure 1A:
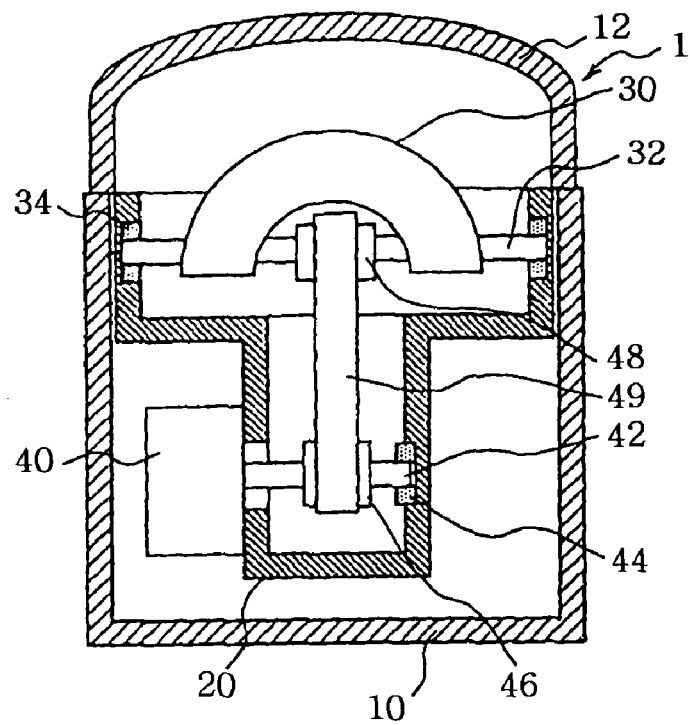
FIG. 1A is a partial cross-sectional view showing an inner structure of a prior art probe of a 3D ultrasonic diagnosis apparatus.
Figure 1B:
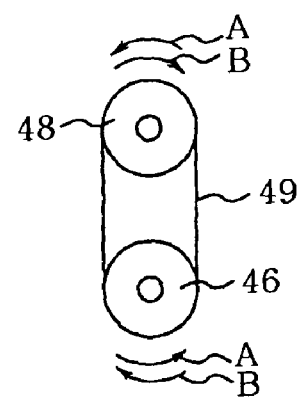
FIG. 1B is a side view showing a power transmitting structure of a prior art probe.
Figure 2:
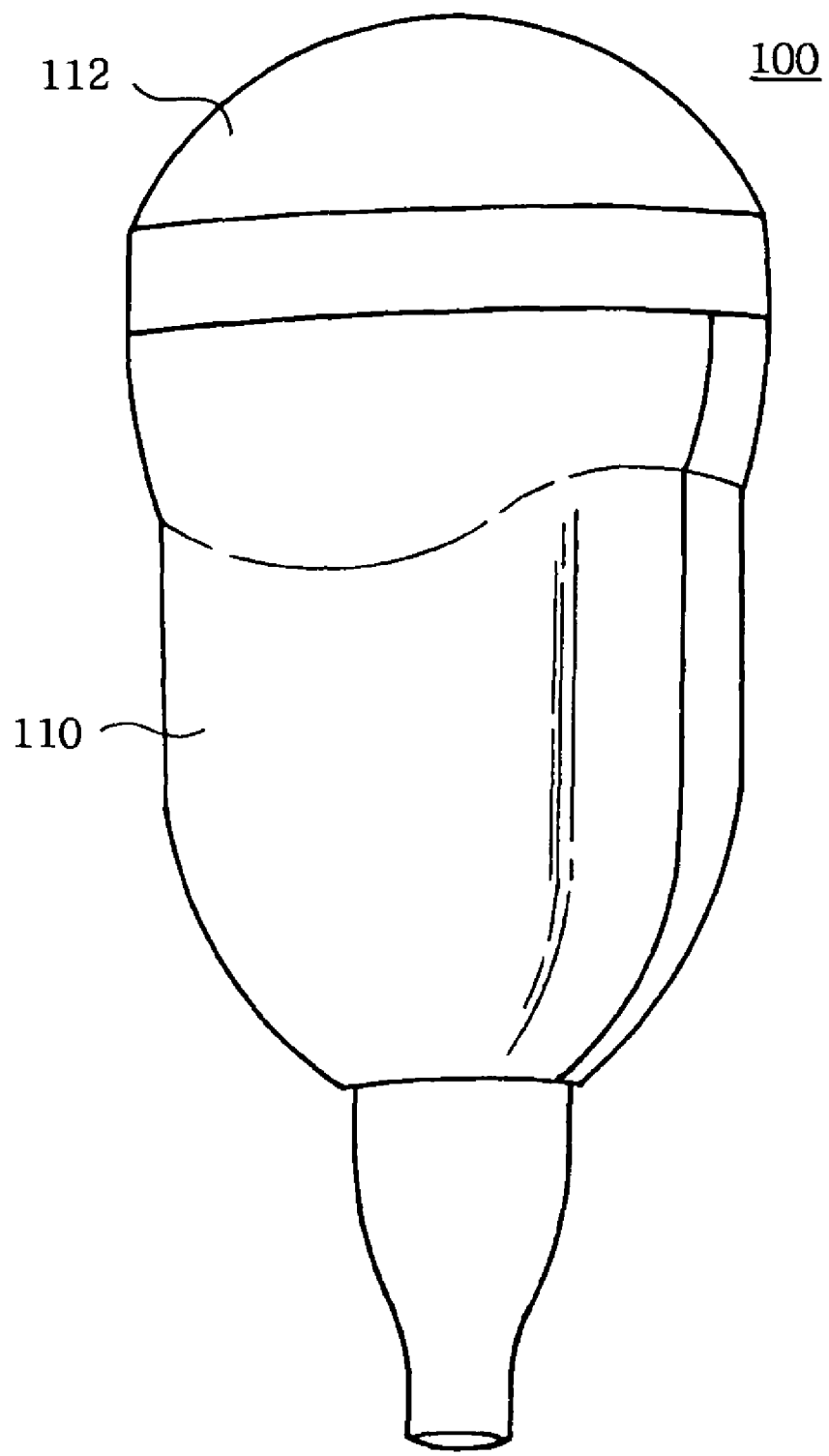
FIG. 2 is a perspective view showing an outer appearance of a probe in an ultrasonic diagnosis apparatus in accordance with the present invention.
Figure 3:
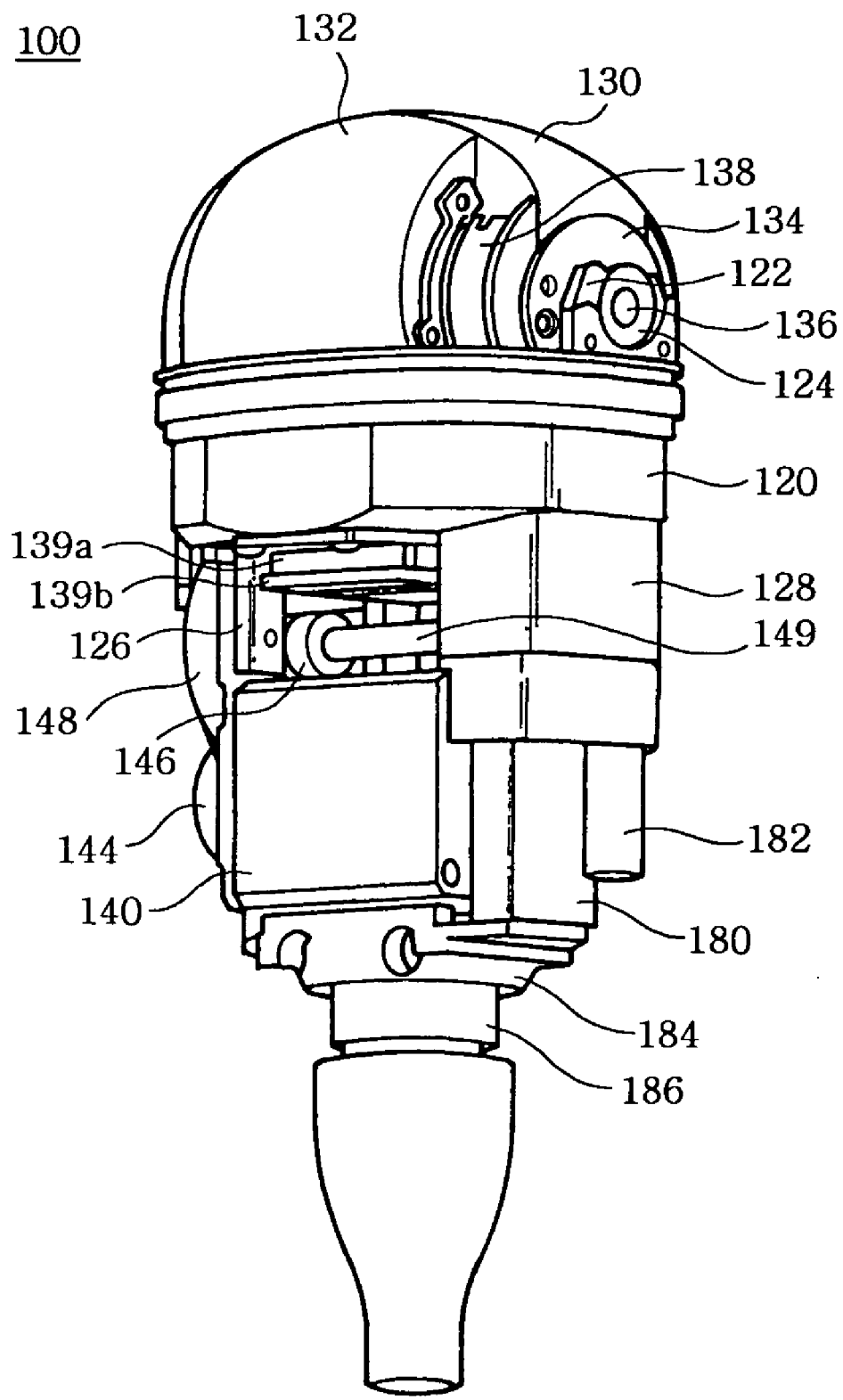
FIG. 3 is a perspective view showing an inner structure of a probe in accordance with the present invention.
Figure 4:
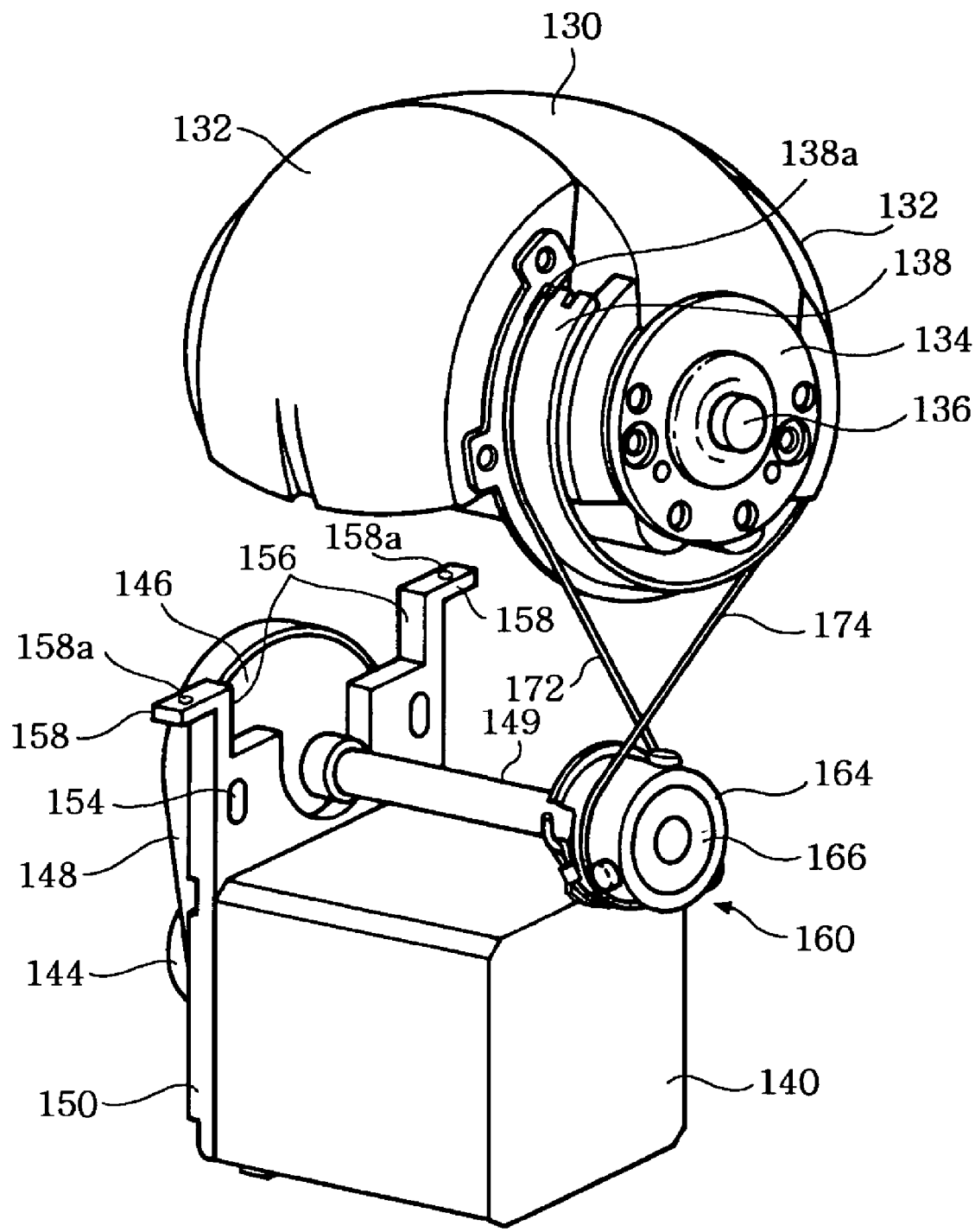
FIG. 4 is a perspective view showing a device for pivoting an ultrasound element assembly of a probe in accordance with the present invention.

FIGS. 2 and 3 are perspective views showing an outer appearance and an inner structure of a probe in an ultrasonic diagnosis apparatus in accordance with the present invention. FIG. 4 is a perspective view showing a device for pivoting an ultrasound element assembly of the probe.

As shown in the drawings, a probe 100 comprises a case 110 having an opened top and a cover 112, which is coupled to the top of the case 110 and is adapted to contact an object to be examined (e.g., a body of a patient). A base 120 is contained in the case 110. An ultrasound element assembly 130 and a transducer 132 for supporting the ultrasound element assembly are pivotably mounted to the base 120. A driving motor 140 for generating power for pivoting the ultrasound element assembly 130 and means for transmitting the power from the motor 40 to the ultrasound element assembly 130 are mounted to the base 120. Preferably, the driving motor 140 is a step motor. This is because the step motor is low in cost and highly reliable, as well as having high torque at low speeds and a simple, rugged construction that operates in almost any environment.

At both ends of the transducer 132 are provided circular holders 134 having pivot shafts 136. A C-shaped wire holder 138 is mounted to one of the pivot shafts 136. One end of each wire rope 172 and 174 is fixed to the wire holder 138, which will be described later. Two opposing shaft holders 122 for supporting the pivot shafts 136 of the transducer holders 134 are formed at the upper edge of the base 120. Bearings 124 for enabling the rotation of the pivot shaft 136 are mounted to the shaft holders 122.

Motor mounting brackets 126 and a receiving part 128, in which a wire rope assembly 160 is contained, are formed integrally at the outer bottom surface of the base 120. Connectors 139a and a PCB (Printed Circuit Board) 139b are mounted to the bottom of the base 120 so as to transmit signals from the ultrasound element assembly 130 to a control unit installed in a main body of the ultrasonic diagnosis apparatus (not shown) through cables (not shown).

A base supporting member 180 is coupled to the outer bottom surface of the receiving part 128 for supporting and shielding the receiving part 128 of the base 120. A tube 182 for injecting an ultrasound-permeable liquid into the base 120 and the cover 112 is provided at the base supporting member 180. A support plate 184 is mounted under the driving motor 140 and the base supporting member 180 in order to support them. A cable guide member 186 for surrounding the cables extending from the PCB 139b to outside the probe is mounted under the support plate 184.

Figure 5:
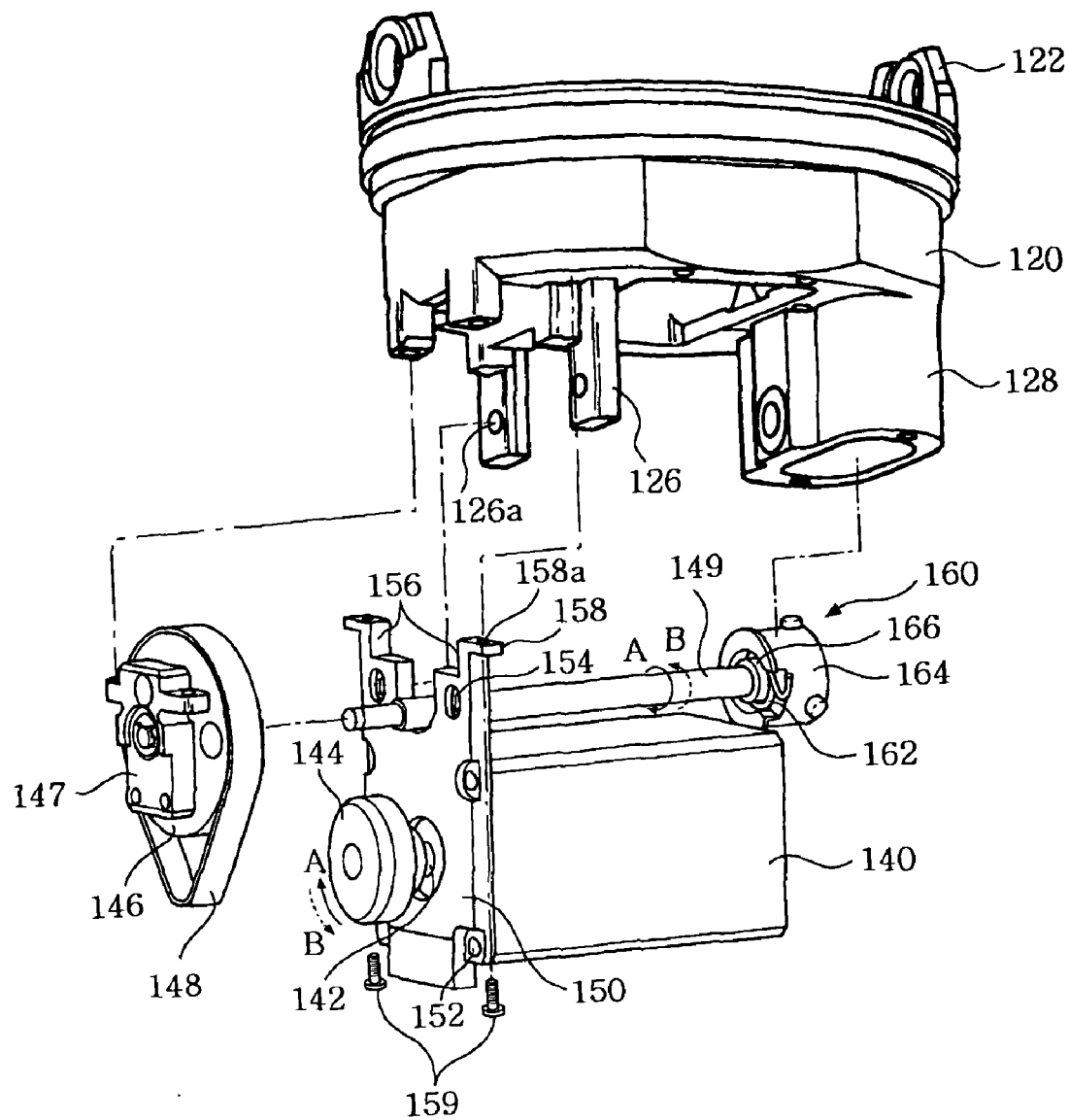
FIG. 5 is an exploded perspective view showing a motor fixing structure.

As shown in FIGS. 4 and 5, the driving motor 140 is disposed such that its driving shaft 142 is directed in the opposite direction to the wire rope assembly 160. A driving pulley 144 is coupled to the front end of the driving shaft 142 of the motor 140. A driven pulley 146 is located above the driving pulley 144. These pulleys 144 and 146 are connected by a timing belt 148 to cooperate with each other. Teeth are formed at the pulleys 144 and 146 and the timing belt 148 so as to prevent any slip therebetween. A driven shaft 149 is fixed to the center of the driven pulley 146 at its one end so as to be rotated together with the driven pulley 146. The other end of the driven shaft 149 is introduced into the receiving part 128 of the base 120 and is coupled to a hub 166 of the wire rope assembly 160. The driving pulley 144 and the driven pulley 146 have predetermined diameters for an adequate speed reduction ratio for pivoting the ultrasound element assembly 130 and the transducer 132. Reference numeral 147 denotes a support plate, to which an end of the driven shaft 149 is coupled. A bearing (not shown) is interposed between the driven shaft 149 and the support plate 147. The support plate 147 is screw-coupled to the outer bottom surface of the base 120 and defines the positions of the driven pulley 146 and the driven shaft 149.

A motor fixing plate 150 for fixing the motor 140 to the base 120 is rectangle in cross-section. The motor fixing plate 150 has first through-holes 152, through which bolts are fastened, to connect the motor 140. The motor fixing plate 150 further has second through-holes 154, through which bolts are fastened to fix the motor fixing plate 150 to the motor fixing brackets 126 of the base 120. A pair of extending portions 156 extends vertically from the upper edge of the motor fixing plate 150. Bending portions 158 are formed horizontally at the tips of the respective extending portions 156 and are directed away from each other. The bending portions 158 have bolt-holes 158a, which are formed vertically.

First, the motor fixing plate 150 is coupled to the motor 140 by tightening the bolts through the first through-holes 152. Then, the motor fixing plate 150 is coupled to the motor fixing brackets 126 of the base 120 by tightening the bolts through the second through-holes 154 of the plate 150 and the bolt-holes 126a of the brackets 126. The support plate 147 for supporting the driven pulley 146 is fixed to the outer bottom surface of the base 120 by using bolts. The timing belt 148 is wound around the driving pulley 144 and the driven pulley 146. Bolts 159 are inserted through the bolt-holes 158a formed at the bending portions 158 of the motor fixing plate 150. Then, as the bolts 159 are tightened toward the outer bottom surface of the base 120 (upward in FIG. 5), the front end of each bolt 159 moves to be placed in contact with the outer bottom surface of the base 120. The reactional force against the movement of the bolt 159 is applied to the motor supporting plate 150. Accordingly, the motor supporting plate 150 and the motor 140 gradually move away from the outer bottom surface of the base 120 (downward in FIG. 5). Thus, the driving pulley 144 also moves away from the driven pulley 146 fixed to the base 120. In order to enable the motor supporting plate 150 to move up and down with respect to the base 120, the second through-holes 154 of the motor supporting plate 150 have a slot-shape, which is long in a vertical direction. By adjusting the distance between the driving pulley 144 and the driven pulley 146 by the above procedure, the tension of the timing belt 148 can be adjusted easily.

Figure 6:
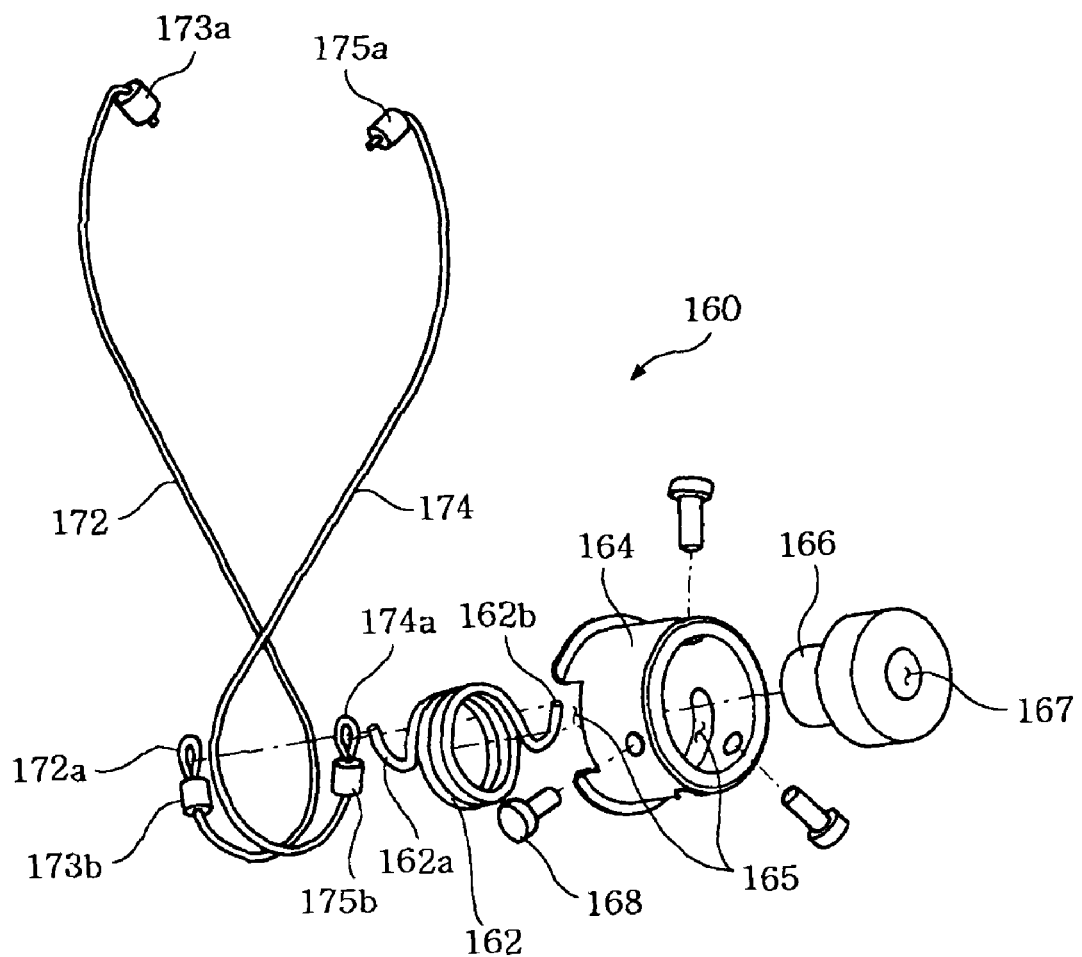
FIG. 6 is an exploded perspective view showing a wire rope assembly.

As shown in FIG. 6, the wire rope assembly 160 includes a torsion coil spring 162, a housing 164, a hub 166 and a pair of wire ropes 172 and 174. The torsion coil spring 162 has U-shaped hook portions 162*a* and 162*b* at its both ends. The housing 164 is formed in a cylindrical shape and contains the torsion coil spring 162. The hub 166 is inserted into the housing 164 so that the torsion coil spring 162 is disposed around the hub 166. One end of each wire rope 172 and 174 is fixed to the wire holder 138, while the other end is hitched by the hook portions 162*a* and 162*b* of the torsion coil spring 162.

The housing 164 has openings 165, through which the hook portions 162*a* and 162*b* of the torsion coil spring 162 are exposed outside the housing 164. The hub 166 has an inserting hole 167 at its center, into which an end of the driven shaft 149 is fitted. The hub 166 is securely fixed in the housing 164 by tightening the bolts 168 through the wall of the housing 164 to be placed in contact with the outer surface of the hub 166.

First tying pieces 173*a* and 175*a* are coupled to first ends of the wire ropes 172 and 174, respectively. The wire holder 138 is provided with slits 138*a*, which allow the wire ropes 172 and 174 to pass through, but restrict the first typing pieces 173*a* and 175*a* to pass through (see FIG. 4). Second tying pieces 173*b* and 175*b* are coupled to second ends of the wire ropes 172 and 174 so as to form knot portions 172*a* and 174*a*. The first tying pieces 173*a* and 175*a* and the second tying pieces 173*b* and 175*b* have one or more holes (not shown), through which the wire ropes 172 and 174 pass. After passing the end portions of the wire ropes 172 and 174 through the holes of the tying pieces 173*a*, 175*a*, 173*b* and 175*b*, an external force is applied to the tying pieces 173*a*, 175*a*, 173*b* and 175*b* to crush them for preventing the wire ropes 172 and 174 from being separated from the tying pieces 173*a*, 175*a*, 173*b* and 175*b*. Preferably, the tying pieces 173*a*, 175*a*, 173*b* and 175*b* are made from a soft metallic material, which is easily deformed by the external force.

Figure 7:
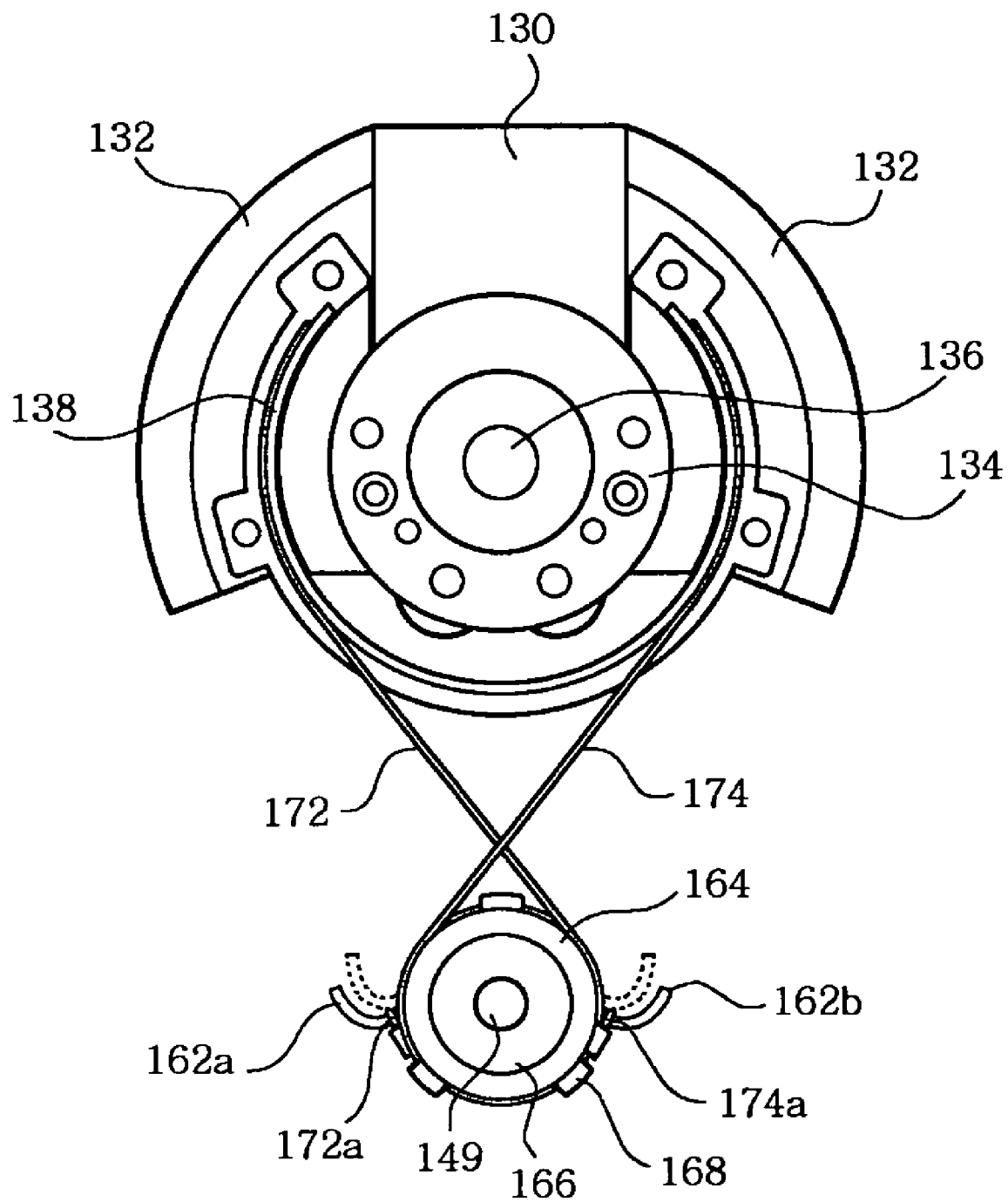
FIG. 7 is a side view showing a connecting structure of a transducer and a wire rope assembly.

As shown in FIG. 7, the first tying pieces 173*a* and 175*a* are caught in the wire holder 138, and the wire ropes 172 and 174 pass through the slits 138*a* of the wire holder 138. Then, the wire ropes 172 and 174 extend toward the wire rope assembly 160 and cross each other in an about 8-shape, and the knot portions 172*a* and 174*a* are respectively hitched by the hook portions 162*a* and 162*b* of the torsion coil spring 162. More specifically, the wire rope 172, the first end of which is caught in the left side of the wire holder 138, extends toward the right side of the housing 164 of the wire rope assembly 160. Then, the wire rope 172 further extends toward the left side of the housing 164 along the outer circumference of the housing 164, and the knot portion 172*a* of the second end of the wire rope 172 is hitched by the left hook portion 162*a* of the torsion coil spring 162. In the same manner, the wire rope 174, the first end of which is caught in the right side of the wire holder 138, extends toward the left side of the housing 164 of the wire rope assembly 160. The wire rope 174 further extends toward the right side of the housing 164 along the outer circumference of the housing 164, and the knot portion 174*a* of the second end of the wire rope 174 is hitched by the right hook portion 162*b* of the torsion coil spring 162. By forming such an 8-shaped arrangement of the wire ropes 172 and 174, both hook portions 162*a* and 162*b* of the torsion coil spring 162 are deformed from first positions (illustrated by dotted lines) to second positions (illustrated by real lines). Therefore, the restoring force of the torsion coil spring 162 is applied evenly to the two wire ropes 172 and 174, thereby making the tensions of the wire ropes 172 and 174 uniform.

Hereinafter, the operational effect of the device for pivoting the ultrasound element assembly of the probe in accordance with the present invention will be described with reference to FIGS. 5, 8A and 8B.

First, before pivoting the ultrasound element assembly 130 for obtaining a 3D ultrasound image, the ultrasound element assembly 130 should be located in a prescribed initial position (typically, the middle position). To this end, the probe 100 transmits the signal of the present position of the ultrasound element assembly 130 to the control unit installed in the main body of the ultrasonic diagnosis apparatus. In response to the signal of the present position of the ultrasound element assembly 130, the control unit controls the device for pivoting the ultrasound element assembly 130 to move the same to the initial position. In this embodiment of the present invention, means for controlling the position of the ultrasound element assembly 130 includes a permanent magnet (not shown) mounted to the transducer 132 and a hall sensor (not shown) mounted to the base 120 for sensing the magnet. Since the device and method for controlling the position of the ultrasound element assembly by using the hall sensor and the magnet are already well known in the art, the explanation thereof is omitted.

Figure 8A:
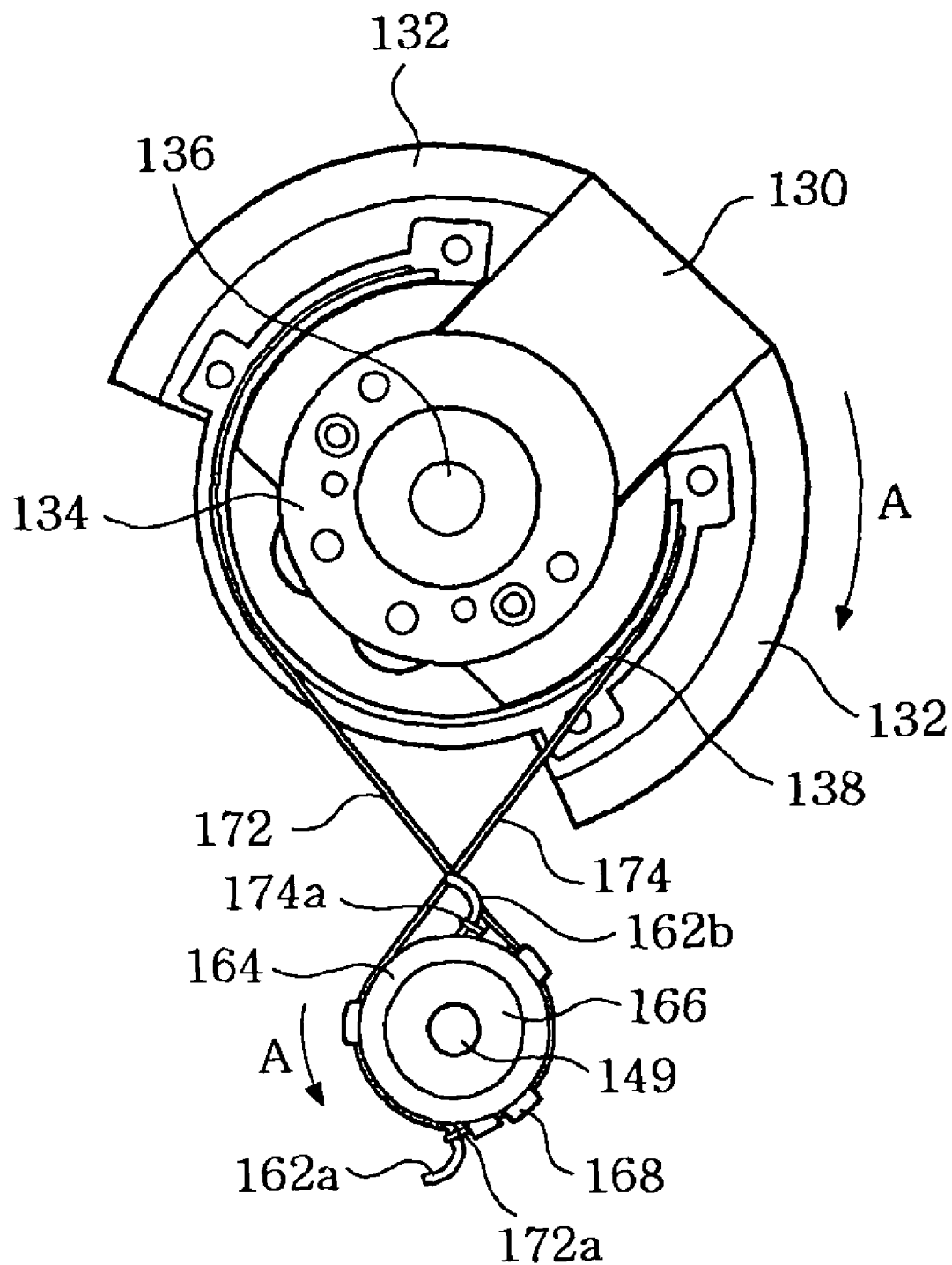
FIGS. 8A and 8B are side views showing the operations of a device for pivoting an ultrasound element assembly of a probe.

After controlling to move the ultrasound element assembly 130 to the initial position, if the driving motor 140 operates to rotate the driving pulley 144, the driven pulley 146 and the driving shaft 149 in a direction of arrow A shown in FIG. 5, then the hub 166 and the housing 164 of the wire rope assembly 160 are also rotated in a direction of arrow A shown in FIG. 8A. At the same time, the torsion coil spring 162, which is located around the hub 166 inside the housing 164, is rotated together with the housing 164. Accordingly, the transducer 132 and the ultrasound element assembly 130 are pivoted in a direction of arrow A by two wire ropes 172 and 174, both ends of which are connected to the hook portions 162*a* and 162*b* of the torsion coil spring 162 and to the wire holder 138.

Figure 8B:
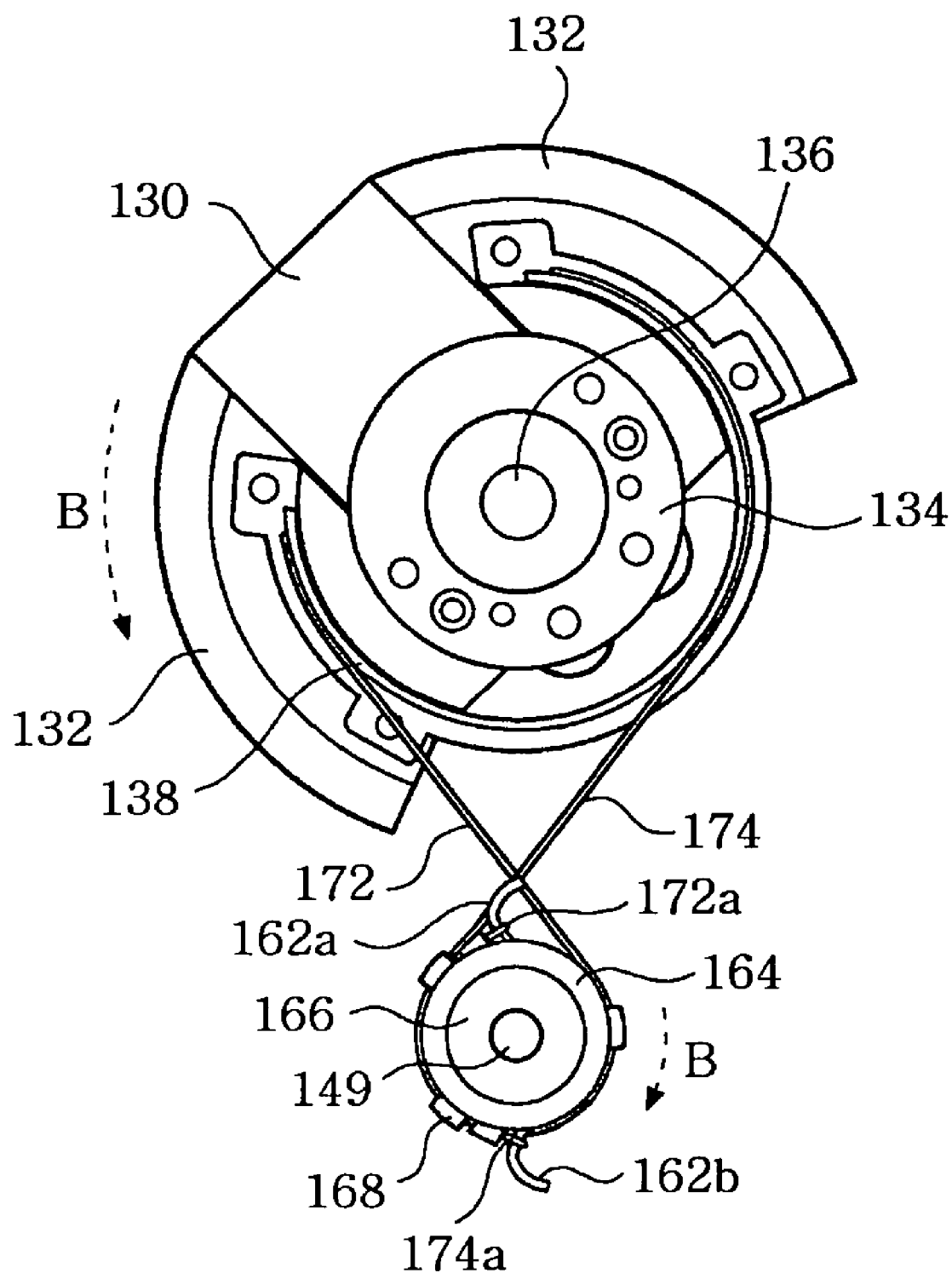

On the contrary, if the driving motor 140 operates to rotate the driving pulley 144, the driven pulley 146 and the driving shaft 149 in a direction of arrow B shown in FIG. 5, then the transducer 132 and the ultrasound element assembly 130 are pivoted in a direction of arrow B shown in FIG. 8B by the above power transmitting structure.

As described above, since the driving pulley and the driven pulley are tooth-engaged with the timing belt and the tension of the wire ropes are maintained uniformly by the torsion coil spring, no slip occurs between these power transmitting elements. Thus, the driving force of the motor can be converted perfectly into the pivoting force of the ultrasound element assembly. Therefore, radiating the ultrasonic wave is regular and the process of obtaining the 3D ultrasound image can be performed smoothly and continuously, thereby increasing the image quality and reducing an error in diagnosis.

Also, although the wire ropes themselves may get loosened due to repeated operations, the tension of the wire ropes are maintained uniform and unchanged by the restoring force of the torsion coil spring, thereby enhancing the operational stability and reliability.

While the present invention has been described and illustrated with respect to a preferred embodiment of the invention, it will be apparent to those skilled in the art that variations and modifications are possible without deviating from the broad principles and teachings of the present invention which should be limited solely by the scope of the claims appended hereto.

What is claimed is:

1. A device for pivoting an ultrasound element assembly of a probe in an ultrasonic diagnosis apparatus, the probe including a base for supporting the ultrasound element assembly, the device comprising:
    a pivot shaft rotatably coupled to the base and supporting the ultrasound element assembly;
    a wire holder coupled to the pivot shaft;
    a driving motor mounted to the base and having a driving shaft; and
    a wire rope assembly including a housing connected to the driving shaft of the driving motor so as to be rotated therewith, the wire rope assembly including a torsion coil spring provided in the housing, the torsion coil spring having a first bent portion at a first end and a second bent portion at a second end, the first and second bent portions extending outside the housing, and the wire rope assembly also including first and second wire ropes, wherein a first end of the first and second wire ropes is connected to the wire holder and a second end of the first and second wire ropes is connected to the first and second bent portions, respectively.

2. The device as recited in claim 1, wherein the first and second wire ropes are arranged to cross with each other.

3. The device as recited in claim 1, wherein the driving motor is a step motor.

4. The device as recited in claim 1, wherein the device further comprises:
    a speed reduction means provided between the driving motor and the wire rope assembly, the speed reduction means including a driving pulley coupled to the driving shaft of the driving motor,
    a driven pulley fixed to the base,
    a timing belt wound around the driving pulley and the driven pulley, and
    a driven shaft, one end of which is fixed to the driven pulley and the other end of which is fixed to the housing of the wire rope assembly.

5. The device as recited in claim 4, wherein teeth are formed at the driving pulley, the driven pulley and the timing belt so that they are tooth-engaged with each other.

6. The device as recited in claim 4, wherein
    a motor supporting plate is coupled to the driving motor near the driving shaft of the driving motor for fixing the driving motor to the base, and
    the motor supporting plate has means for adjusting a tension of the timing belt by adjusting the distance between the driving pulley and the driven pulley.

7. The device as recited in claim 6, wherein the means for adjusting the tension of the timing belt includes at least one through-hole, through which a bolt is fastened to fix the motor supporting plate to the base, extending portions extending vertically from the motor fixing plate, bending portions formed horizontally at the tips of the respective extending portions, and bolt-holes formed vertically at the bending portions, whereby as bolts are tightened through the bolt-holes toward the base, a front end of each bolt moves to be in contact with the base and a reactional force against the movement of the bolt is applied to the motor supporting plate, thereby causing the driving pulley to move away from the driven pulley.

8. The device as recited in claim 7, wherein the through-hole has a slot-shape, which is long in a vertical direction.

* * * * *